(12) United States Patent
Leven et al.

(10) Patent No.: US 9,878,148 B2
(45) Date of Patent: Jan. 30, 2018

(54) LEAD WITH CONTACT END CONDUCTOR GUIDE AND METHODS OF MAKING AND USING

(71) Applicant: BOSTON SCIENTIFIC NEUROMODULATION CORPORATION, Valencia, CA (US)

(72) Inventors: Jacob B. Leven, Huntington Beach, CA (US); Anne Margaret Pianca, Santa Monica, CA (US); John Michael Barker, Ventura, CA (US); Geoffrey Abellana Villarta, Valencia, CA (US); Milad Girgis, North Hills, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 790 days.

(21) Appl. No.: 13/864,049

(22) Filed: Apr. 16, 2013

(65) Prior Publication Data
US 2013/0274844 A1  Oct. 17, 2013

Related U.S. Application Data

(60) Provisional application No. 61/625,587, filed on Apr. 17, 2012, provisional application No. 61/745,354, filed on Dec. 21, 2012.

(51) Int. Cl.
*A61N 1/05* (2006.01)
(52) U.S. Cl.
CPC ....... *A61N 1/0551* (2013.01); *Y10T 29/49169* (2015.01)

(58) Field of Classification Search
USPC ............................................. 607/116; 29/854
See application file for complete search history.

(56) References Cited

U.S. PATENT DOCUMENTS

| | | | | |
|---|---|---|---|---|
| 5,330,522 | A * | 7/1994 | Kreyenhagen | 607/122 |
| 5,554,176 | A * | 9/1996 | Maddison et al. | 607/9 |
| 5,584,873 | A * | 12/1996 | Shoberg et al. | 607/122 |
| 5,855,552 | A * | 1/1999 | Houser et al. | 600/374 |
| 5,865,843 | A * | 2/1999 | Baudino | 607/116 |
| 5,893,885 | A * | 4/1999 | Webster, Jr. | 607/122 |

(Continued)

OTHER PUBLICATIONS

U.S. Appl. No. 12/177,823, filed Jul. 22, 2008.
(Continued)

*Primary Examiner* — Carl H Layno
*Assistant Examiner* — Erin M Piateski
(74) *Attorney, Agent, or Firm* — Lowe Graham Jones PLLC; Bruce E. Black

(57) ABSTRACT

An electrical stimulation lead includes a cog-shaped conductor guide disposed either at the proximal end or the distal end of the lead. The cog-shaped conductor guide includes a central core and multiple protrusions extending outwards from the core. Conductor tracks are defined within the cog-shaped conductor guide between adjacent protrusions. Electrodes are provided along the distal end of the lead, terminals are provided along the proximal end of the lead, and conductors couple the electrodes to the terminals. An elongated lead body extends from the electrodes to the terminals of the lead. Each of the conductors has an end portion positioned within one of the conductor tracks of the cog-shaped conductor guide.

19 Claims, 10 Drawing Sheets

(56) References Cited

U.S. PATENT DOCUMENTS

| | | |
|---|---|---|
| 6,181,969 B1 | 1/2001 | Gord |
| 6,181,971 B1* | 1/2001 | Doan .................... 607/116 |
| 6,304,784 B1* | 10/2001 | Allee et al. ................ 607/116 |
| 6,516,227 B1 | 2/2003 | Meadows et al. |
| 6,609,029 B1 | 8/2003 | Mann et al. |
| 6,609,032 B1 | 8/2003 | Woods et al. |
| 6,741,892 B1 | 5/2004 | Meadows et al. |
| 7,006,859 B1* | 2/2006 | Osorio et al. ............... 600/378 |
| 7,244,150 B1 | 7/2007 | Brase et al. |
| 7,437,193 B2 | 10/2008 | Parramon et al. |
| 7,450,997 B1 | 11/2008 | Pianca et al. |
| 7,672,734 B2 | 3/2010 | Anderson et al. |
| 7,761,165 B1 | 7/2010 | He et al. |
| 7,783,359 B2 | 8/2010 | Meadows |
| 7,792,590 B1 | 9/2010 | Pianca et al. |
| 7,809,446 B2 | 10/2010 | Meadows |
| 7,949,395 B2 | 5/2011 | Kuzma |
| 7,974,706 B2 | 7/2011 | Moffitt et al. |
| 8,224,460 B2 | 5/2012 | He |
| 8,224,450 B2 | 7/2012 | Brase |
| 8,271,094 B1 | 9/2012 | Moffitt et al. |
| 8,295,944 B2 | 10/2012 | Howard et al. |
| 8,364,278 B2 | 1/2013 | Pianca et al. |
| 8,391,935 B2 | 3/2013 | McDonald |
| 2001/0018607 A1* | 8/2001 | Borgersen et al. ........... 607/121 |
| 2003/0204232 A1* | 10/2003 | Sommer et al. ............. 607/122 |
| 2004/0064024 A1* | 4/2004 | Sommer ...................... 600/374 |
| 2004/0097965 A1* | 5/2004 | Gardeski et al. ............ 606/129 |
| 2005/0027342 A1 | 2/2005 | Shoberg et al. |
| 2005/0222659 A1* | 10/2005 | Olsen et al. .................. 607/116 |
| 2006/0089691 A1* | 4/2006 | Kaplan et al. ............... 607/116 |
| 2007/0150036 A1 | 6/2007 | Anderson |
| 2007/0197892 A1* | 8/2007 | Shen et al. ................... 600/378 |
| 2007/0293922 A1* | 12/2007 | Soltis et al. ................. 607/122 |
| 2008/0004618 A1* | 1/2008 | Johnson et al. .............. 606/41 |
| 2009/0187222 A1 | 7/2009 | Barker |
| 2009/0198312 A1* | 8/2009 | Barker ......................... 607/116 |
| 2009/0222073 A1* | 9/2009 | Flowers et al. .............. 607/116 |
| 2009/0276021 A1 | 11/2009 | Meadows et al. |
| 2010/0076535 A1 | 3/2010 | Pianca et al. |
| 2010/0137928 A1* | 6/2010 | Duncan et al. ............... 607/5 |
| 2010/0268298 A1 | 10/2010 | Moffitt et al. |
| 2010/0298761 A1* | 11/2010 | Staal et al. .................... 604/20 |
| 2010/0306997 A1* | 12/2010 | Pardo et al. .................. 29/825 |
| 2011/0004267 A1 | 1/2011 | Meadows |
| 2011/0005069 A1 | 1/2011 | Pianca |
| 2011/0078900 A1 | 4/2011 | Pianca et al. |
| 2011/0130817 A1 | 6/2011 | Chen |
| 2011/0130818 A1 | 6/2011 | Chen |
| 2011/0196229 A1* | 8/2011 | Weiss et al. .................. 600/423 |
| 2011/0238129 A1 | 9/2011 | Moffitt et al. |
| 2011/0313500 A1 | 12/2011 | Barker et al. |
| 2012/0016378 A1 | 1/2012 | Pianca et al. |
| 2012/0046710 A1 | 2/2012 | DiGiore et al. |
| 2012/0071949 A1 | 3/2012 | Pianca et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2012/0232629 A1* | 9/2012 | Bloemer et al. ............. 607/116 |

OTHER PUBLICATIONS

U.S. Appl. No. 61/022,953, filed Jan. 23, 2008.
U.S. Appl. No. 61/170,037, filed Apr. 16, 2009.
U.S. Appl. No. 61/316,759, filed Mar. 23, 2010.
U.S. Appl. No. 61/494,247, filed Jun. 7, 2011.
U.S. Appl. No. 61/554,861, filed Nov. 2, 2011.
U.S. Appl. No. 61/591,046, filed Jan. 26, 2012.
U.S. Appl. No. 61/625,587, filed Apr. 17, 2012.
Official Communication for U.S. Appl. No. 13/864,030 dated Mar. 19, 2014.
Official Communication for U.S. Appl. No. 13/864,030 dated Dec. 23, 2014.

* cited by examiner

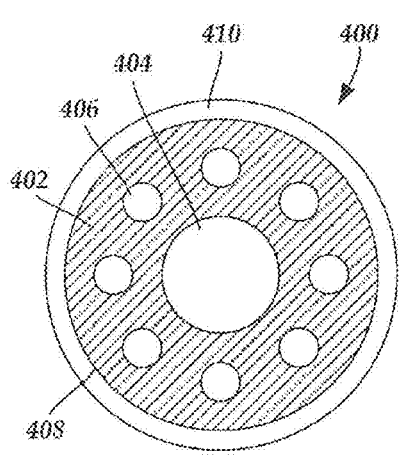
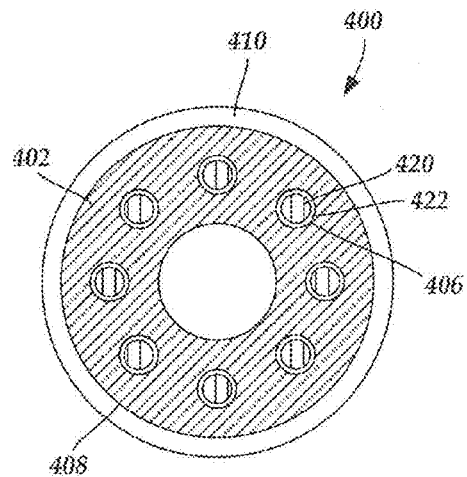
Fig. 4A  Fig. 4B
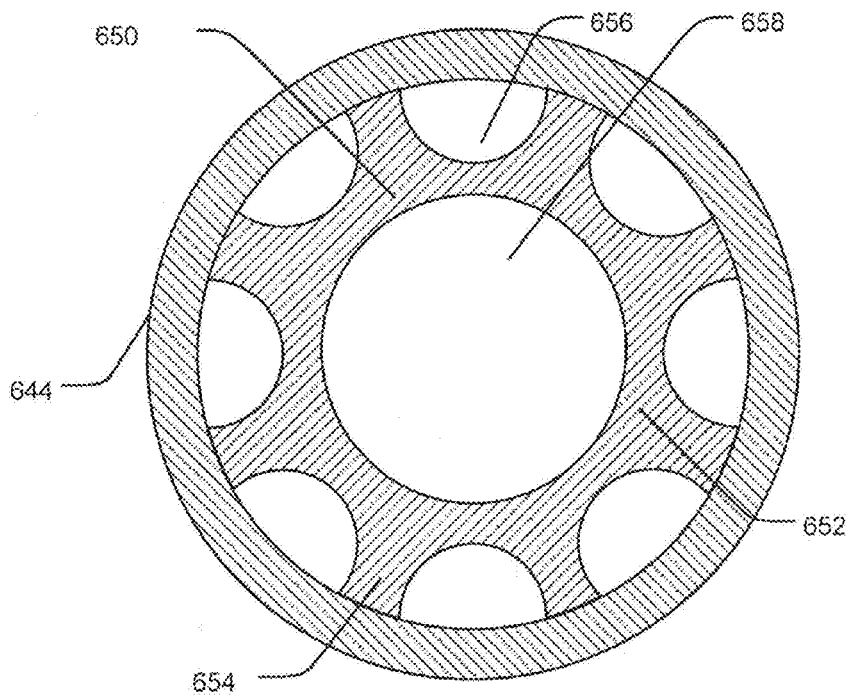
Fig. 6

LEAD WITH CONTACT END CONDUCTOR GUIDE AND METHODS OF MAKING AND USING

CROSS-REFERENCE TO RELATED APPLICATIONS

This application claims the benefit under 35 U.S.C. § 119(e) of U.S. Provisional Patent Application Ser. No. 61/625,587 filed on Apr. 17, 2012, and U.S. Provisional Patent Application Ser. No. 61/745,354 filed on Dec. 21, 2012, which are incorporated herein by reference.

FIELD

The present invention is directed to the area of implantable electrical stimulation systems and methods of making and using the systems. The present invention is also directed to implantable electrical stimulation leads having a separate end conductor guide for contacts, as well as methods of making and using the leads and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is an electrical stimulation lead having a proximal end and a distal end. The lead includes a cog-shaped conductor guide is disposed either at the proximal end or the distal end of the lead. The cog-shaped conductor guide includes a central core and multiple protrusions extending outwards from the core. A number of conductor tracks are defined within the cog-shaped conductor guide between adjacent protrusions of the cog-shaped conductor guide. Further, multiple electrodes are provided along the distal end of the lead. These electrodes are disposed over the cog-shaped conductor guide, when the cog-shaped conductor guide is disposed at the distal end of the lead. A number of terminals are disposed along the proximal end of the lead. In a case where the cog-shaped conductor guide is disposed at the proximal end of the lead, the terminals are disposed over the cog-shaped conductor guide. An elongated lead body extends from the electrodes to the terminals of the lead. Multiple conductors couple the electrodes to the terminals. Each of the conductors has an end portion positioned within one of the conductor tracks of the cog-shaped conductor guide.

Another embodiment is an electrical stimulation lead having a proximal end and a distal end. An end conductor guide is disposed either at the proximal end or the distal end of the lead. The end conductor guide has a generally cylindrical shape and a number of conductor tracks are formed over an exterior surface of the end conductor guide. Each of the conductor tracks extends longitudinally from a first end of the end conductor guide at least partway along the length of the end conductor guide. Protrusions are disposed between adjacent conductor tracks of the end conductor guide, providing it a cog-shaped cross-section at its first end. Electrodes are provided along the distal end of the lead. These electrodes are disposed over the end conductor guide, when the end conductor guide is disposed at the distal end of the lead. Terminals are provided along the proximal end of the lead. If the end conductor guide is disposed at the proximal end of the lead, then the terminals are disposed over the end conductor guide. The lead further includes an elongated lead body that extends from the electrodes to the terminals. Conductors couple the electrodes to the terminals. Each of the conductors has an end portion positioned within one of the conductor tracks of the end conductor guide.

Yet another embodiment is a method of making an electrical stimulation lead including providing a cog-shaped conductor guide having a central core and protrusions extending outward from the central core. Conductor tracks are defined within the conductor guide between adjacent protrusions of the conductor guide. The method further includes disposing end portions of each of a plurality of conductors in the conductor tracks of the cog-shaped conductor guide; disposing a plurality of contacts over the cog-shaped conductor guide; coupling the end portions of the conductors to the plurality of contacts; and disposing insulative spacers between adjacent contacts

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 4A is a transverse cross-sectional view of one embodiment of the lead of FIG. 3, the lead including a multi-lumen conductor guide that defines a central lumen and a plurality of conductor lumens arranged around the central lumen, according to the invention;

FIG. 4B is a transverse cross-sectional view of one embodiment of conductors disposed in each of a plurality of conductor lumens of the multi-lumen conductor guide of FIG. 4A such that a different single conductor is disposed in each of the conductor lumens, according to the invention;

FIG. 6 is a schematic cross-sectional view of the arrangement of FIG. 5E, according to the invention;

DETAILED DESCRIPTION

The present invention is directed to the area of implantable electrical stimulation systems and methods of making and using the systems. The present invention is also directed to implantable electrical stimulation leads having a separate end conductor guide for contacts, as well as methods of making and using the leads and electrical stimulation systems.

Suitable implantable electrical stimulation systems include, but are not limited to, at least one lead with one or more electrodes disposed along a distal end of the lead and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; 7,761,165; 7,974,706; 8,175,710; 8,224,450; and 8,364,278; and U.S. Patent Application Publication No. 2007/0150036, all of which are incorporated by reference.

Figure 1:
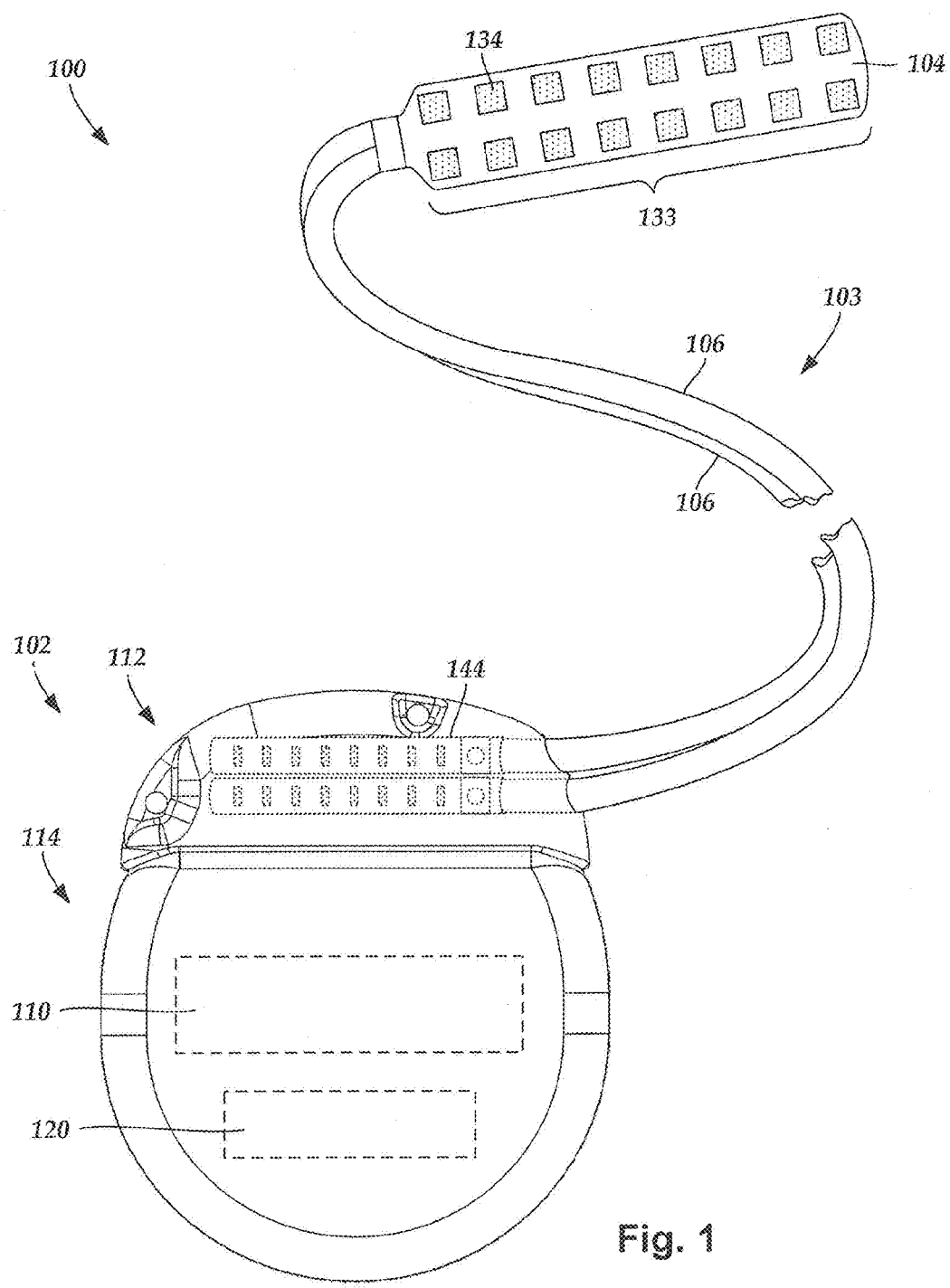
FIG. 1 is a schematic side view of one embodiment of an electrical stimulation system that includes a paddle lead electrically coupled to a control module, according to the invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes a paddle body 104 and one or more lead bodies 106. In FIG. 1, the lead 103 is shown having two lead bodies 106. It will be understood that the lead 103 can include any suitable number of lead bodies including, for example, one, two, three, four, five, six, seven, eight or more lead bodies 106. An array of electrodes 133, such as electrode 134, is disposed on the paddle body 104, and an array of terminals (e.g., 210 in FIG. 3A-3B) is disposed along each of the one or more lead bodies 106.

It will be understood that the electrical stimulation system can include more, fewer, or different components and can have a variety of different configurations including those configurations disclosed in the electrical stimulation system references cited herein. For example, instead of a paddle body, the electrodes can be disposed in an array at or near the distal end of a lead body forming a percutaneous lead.

Figure 2A:
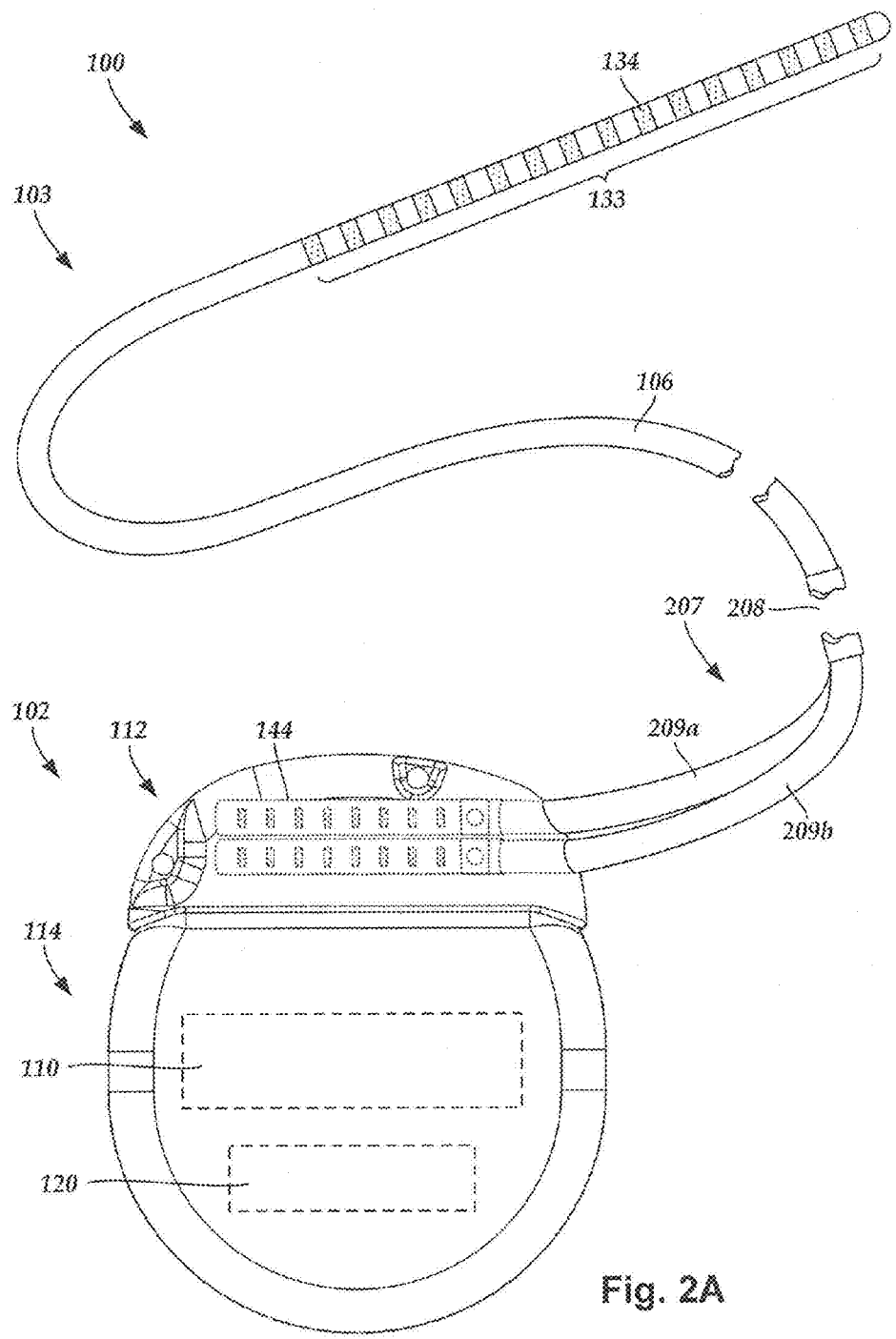
FIG. 2A is a schematic side view of one embodiment of an electrical stimulation system that includes a percutaneous lead electrically coupled to a control module, according to the invention.
Figure 2B:
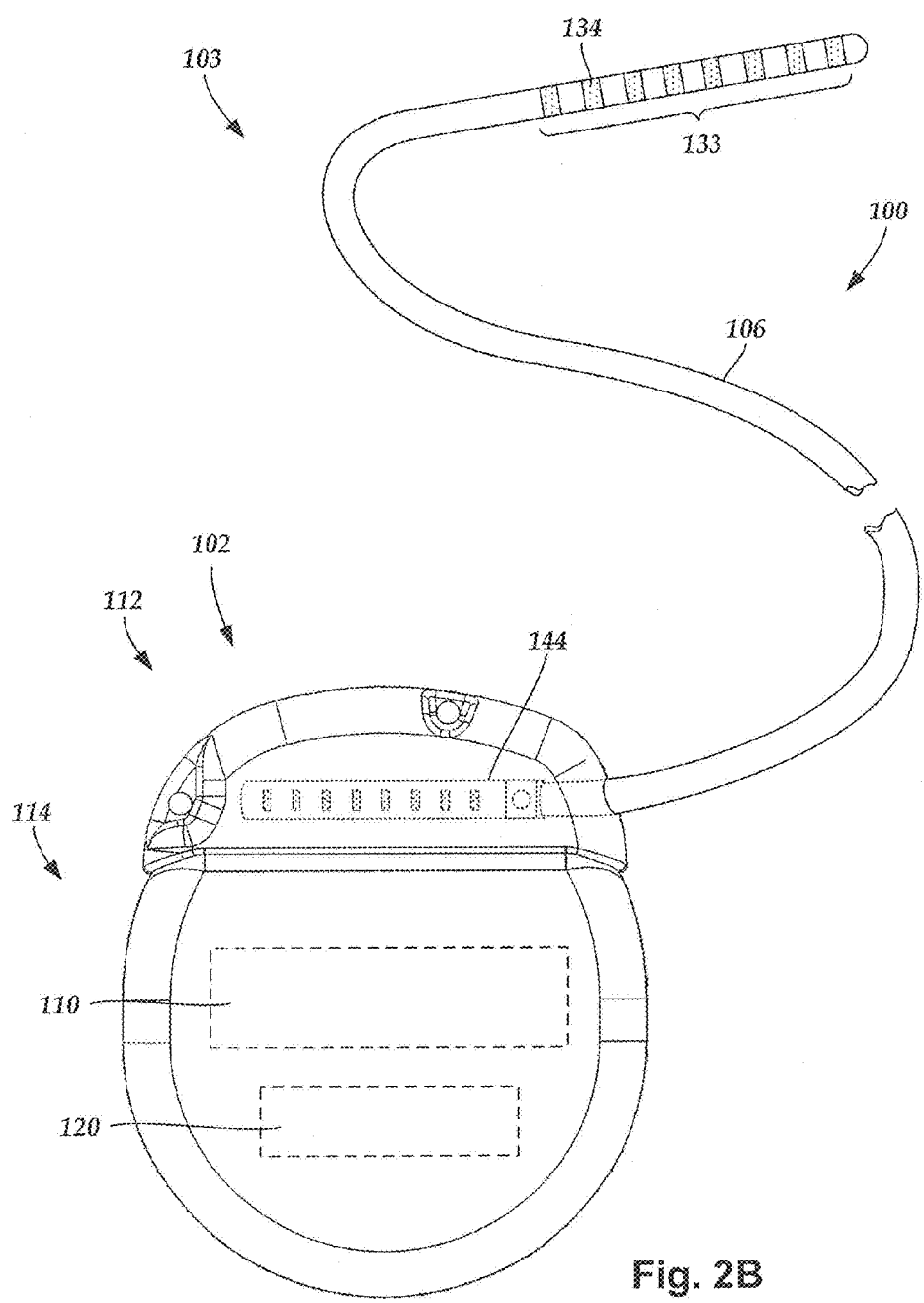
FIG. 2B is a schematic side view of another embodiment of an electrical stimulation system that includes a percutaneous lead electrically coupled to a control module, according to the invention.

FIGS. 2A and 2B illustrate schematically additional embodiments of the electrical stimulation system 100, where the lead 103 is a percutaneous lead. In FIGS. 2A and 2B, the electrodes 134 are shown disposed along the one or more lead bodies 106. In at least some embodiments, the lead 103 is isodiametric along a longitudinal length of the lead body 106.

The lead 103 can be coupled to the control module 102 in any suitable manner. In FIG. 1, the lead 103 is shown coupling directly to the control module 102. In at least some other embodiments, the lead 103 couples to the control module 102 via one or more intermediate devices (300 in FIGS. 3A-3B). For example, in at least some embodiments one or more lead extensions 324 (see e.g., FIG. 3B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

In FIG. 2A, the electrical stimulation system 100 is shown having a splitter 207 configured and arranged for facilitating coupling of the lead 103 to the control module 102. The splitter 207 includes a splitter connector 208 configured to couple to a proximal end of the lead 103, and one or more splitter tails 209a and 209b configured and arranged to couple to the control module 102 (or another splitter, a lead extension, an adaptor, or the like).

The control module 102 typically includes a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including the paddle body 104, the one or more of the lead bodies 106, and the control module 102, are typically implanted into the body of a patient. The electrical stimulation system can be used for a variety of applications including, but not limited to deep brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium.

Any suitable number of electrodes 134 can be disposed on the lead including, for example, four, five, six, seven, eight, nine, ten, eleven, twelve, fourteen, sixteen, twenty-four, thirty-two, or more electrodes 134. In the case of paddle leads, the electrodes 134 can be disposed on the paddle body 104 in any suitable arrangement. In FIG. 1, the electrodes 134 are arranged into two columns, where each column has eight electrodes 134.

The electrodes of the paddle body 104 (or one or more lead bodies 106) are typically disposed in, or separated by, a non-conductive, biocompatible material such as, for example, silicone, polyurethane, polyetheretherketone ("PEEK"), epoxy, and the like or combinations thereof. The one or more lead bodies 106 and, if applicable, the paddle body 104 and may be formed in the desired shape by any process including, for example, molding (including injection molding), casting, and the like. The non-conductive material typically extends from the distal ends of the one or more lead bodies 106 to the proximal end of each of the one or more lead bodies 106.

In the case of paddle leads, the non-conductive material typically extends from the paddle body 104 to the proximal end of each of the one or more lead bodies 106. Additionally, the non-conductive, biocompatible material of the paddle body 104 and the one or more lead bodies 106 may be the same or different. Moreover, the paddle body 104 and the one or more lead bodies 106 may be a unitary structure or can be formed as two separate structures that are permanently or detachably coupled together.

Figure 3A:
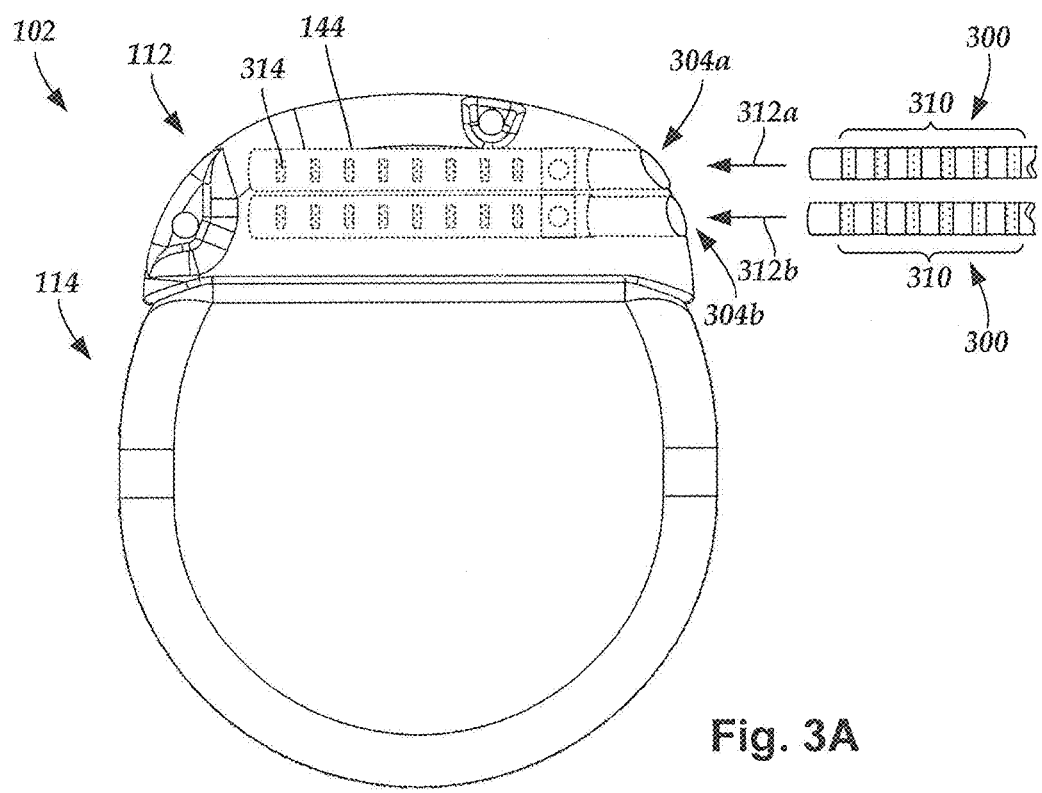
FIG. 3A is a schematic view of one embodiment of the control module of FIG. 1 configured and arranged to electrically couple to an elongated device, according to the invention.
Figure 3B:
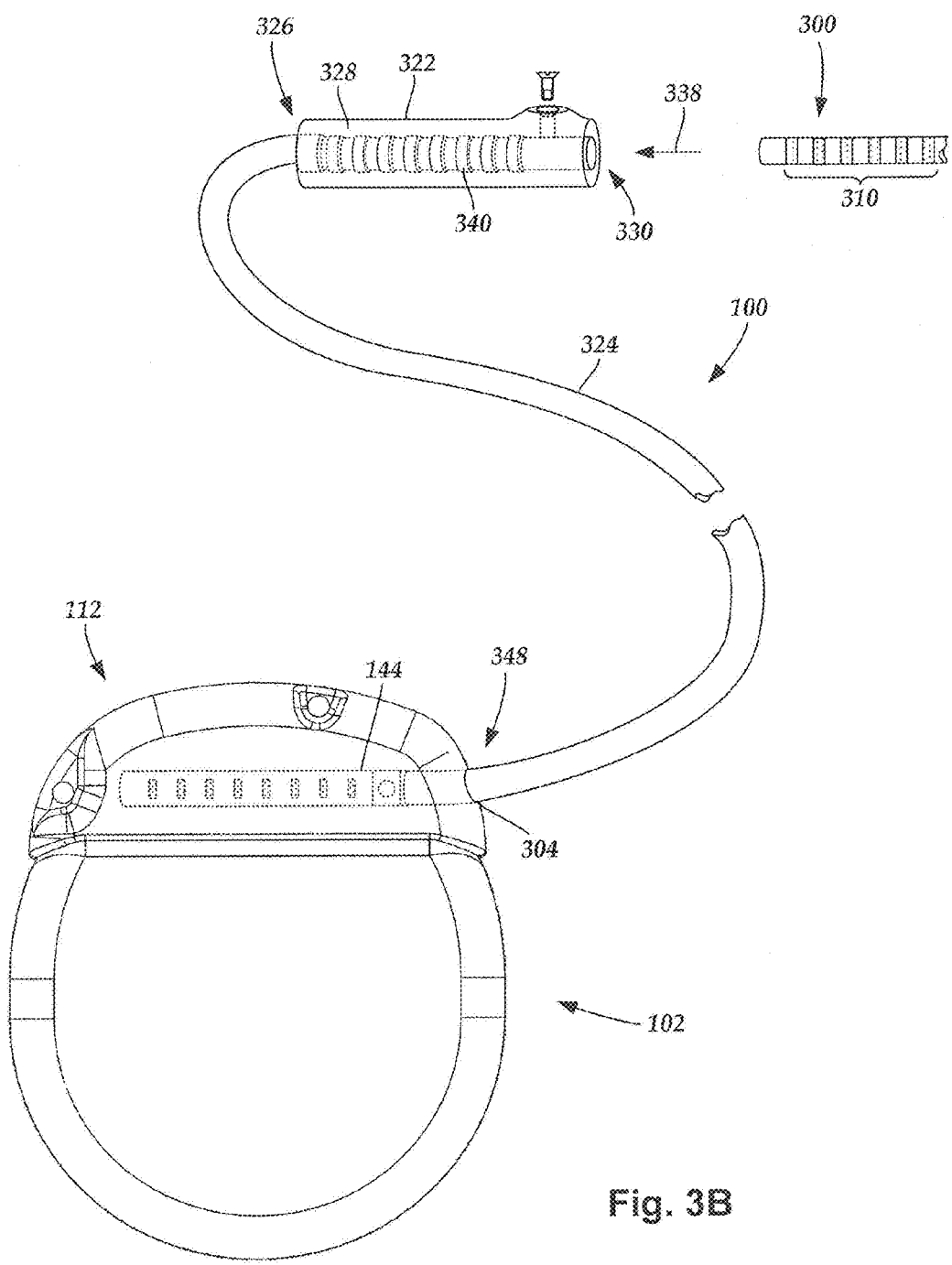
FIG. 3B is a schematic view of one embodiment of a lead extension configured and arranged to electrically couple the elongated device of FIG. 3A to the control module of FIG. 1, according to the invention.

Terminals (e.g., 310 in FIGS. 3A-3B) are typically disposed along the proximal end of the one or more lead bodies 106 of the electrical stimulation system 100 (as well as any splitters, lead extensions, adaptors, or the like) for electrical connection to corresponding connector contacts (e.g., 314 in FIGS. 3A-3B). The connector contacts are disposed in connectors (e.g., 144 in FIGS. 1-3B; and 322 FIG. 3B) which in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors may extend through a lumen. There may also be one or more lumens (not shown) that open at, or near, the proximal end of the one or more lead bodies 106, for example, for inserting a stylet to facilitate placement of the one or more lead bodies 106 within a body of a patient. Additionally, there may also be one or more lumens (not shown) that open at, or near, the distal end of the one or more lead bodies 106, for example, for infusion of drugs or medication into the site of implantation of the one or more lead bodies 106. In at least one embodiment, the one or more lumens are flushed continually, or on a regular basis, with saline, epidural fluid, or the like. In at least some embodiments, the one or more lumens can be permanently or removably sealable at the distal end.

FIG. 3A is a schematic side view of one embodiment of a proximal end of one or more elongated devices 300 configured and arranged for coupling to one embodiment of the control module connector 144. The one or more elongated devices may include, for example, one or more of the lead bodies 106 of FIG. 1, one or more intermediate devices (e.g., a splitter, the lead extension 324 of FIG. 3B, an adaptor, or the like or combinations thereof), or a combination thereof.

The control module connector 144 defines at least one port into which a proximal end of the elongated device 300 can be inserted, as shown by directional arrows 312a and 312b. In FIG. 3A (and in other figures), the connector housing 112 is shown having two ports 304a and 304b. The connector housing 112 can define any suitable number of ports including, for example, one, two, three, four, five, six, seven, eight, or more ports.

The control module connector 144 also includes a plurality of connector contacts, such as connector contact 314, disposed within each port 304a and 304b. When the elongated device 300 is inserted into the ports 304a and 304b, the connector contacts 314 can be aligned with a plurality of terminals 310 disposed along the proximal end(s) of the elongated device(s) 300 to electrically couple the control module 102 to the electrodes (134 of FIG. 1) disposed on the paddle body 104 of the lead 103. Examples of connectors in control modules are found in, for example, U.S. Pat. No. 7,244,150 and U.S. Pat. No. 8,224,450, which are incorporated by reference.

FIG. 3B is a schematic side view of another embodiment of the electrical stimulation system 100. The electrical stimulation system 100 includes a lead extension 324 that is configured and arranged to couple one or more elongated devices 300 (e.g., one of the lead bodies 106 of FIGS. 1, 2A, and 2B, the splitter 207 of FIG. 2A, an adaptor, another lead extension, or the like or combinations thereof) to the control module 102. In FIG. 3B, the lead extension 324 is shown coupled to a single port 304 defined in the control module connector 144. Additionally, the lead extension 324 is shown configured and arranged to couple to a single elongated device 300. In alternate embodiments, the lead extension 324 is configured and arranged to couple to multiple ports 304 defined in the control module connector 144, or to receive multiple elongated devices 300, or both.

A lead extension connector 322 is disposed on the lead extension 324. In FIG. 3B, the lead extension connector 322 is shown disposed at a distal end 326 of the lead extension 324. The lead extension connector 322 includes a connector housing 328. The connector housing 328 defines at least one port 330 into which terminals 310 of the elongated device 300 can be inserted, as shown by directional arrow 338. The connector housing 328 also includes a plurality of connector contacts, such as connector contact 340. When the elongated device 300 is inserted into the port 330, the connector contacts 240 disposed in the connector housing 328 can be aligned with the terminals 310 of the elongated device 300 to electrically couple the lead extension 324 to the electrodes (134 of FIGS. 1, 2A, and 2B) disposed along the lead (103 in FIGS. 1, 2A, and 2B).

In at least some embodiments, the proximal end of the lead extension 324 is similarly configured and arranged as a proximal end of the lead 103 (or other elongated device 300). The lead extension 324 may include a plurality of electrically conductive wires (not shown) that electrically couple the connector contacts 340 to a proximal end 348 of the lead extension 324 that is opposite to the distal end 326. In at least some embodiments, the conductive wires disposed in the lead extension 324 can be electrically coupled to a plurality of terminals (not shown) disposed along the proximal end 348 of the lead extension 324. In at least some embodiments, the proximal end 348 of the lead extension 324 is configured and arranged for insertion into a connector disposed in another lead extension (or another intermediate device). In other embodiments (and as shown in FIG. 3B), the proximal end 348 of the lead extension 324 is configured and arranged for insertion into the control module connector 144.

Turning to FIG. 4A, in at least some embodiments, the lead includes a lead body with an elongated multi-lumen conductor guide having multiple conductor lumens arranged about a central lumen. In at least some embodiments, the conductor lumens are arranged about the central lumen such that there are no other lumens extending along the multi-lumen conductor guide between the central lumen and each of the multiple conductor lumens. The conductor lumens include at least one helical section forming an enclosed pathway around at least a portion of the central lumen. In some embodiments, the conductor lumens are each configured and arranged to receive a single conductor. In other embodiments, at least one of the conductor lumens is configured and arranged to receive multiple conductors.

FIG. 4A is a transverse cross-sectional view of one embodiment of the lead 400. The lead 400 includes an elongated multi-lumen conductor guide 402. Examples of the multi-lumen conductor guide can be found in the earlier cited patents and patent applications, as well as U.S. Provisional Patent Application Ser. No. 61/625,587, incorporated herein by reference. The multi-lumen conductor guide 402 may extend an entire longitudinal length of the lead 400 between the electrodes (134 of FIGS. 1, 2A, and 2B) to the terminals (310 of FIGS. 3A and 3B). As shown in FIG. 4A, the multi-lumen conductor guide 402 defines a central lumen 404 and a plurality of conductor lumens, such as a conductor lumen 406. The conductor lumen can have any suitable cross-sectional shape (e.g., round, oval, rectangular, triangular, or the like).

In at least some embodiments, the plurality of conductor lumens 406 are encapsulated by the multi-lumen conductor guide 402 such that the conductor lumens 406 do not extend to an outer surface 408 of the multi-lumen conductor guide 402. In a case, when conductors (420 in FIG. 4B) are disposed in the conductor lumens 406, the conductors are not exposed along the outer surface 408 of the multi-lumen conductor guide 402. The central lumen 404 and the plurality of conductor lumens 406 can be arranged in any suitable manner. In preferred embodiments, the conductor lumens 406 are disposed in the multi-lumen conductor guide 402 such that the conductor lumens 406 are peripheral to the central lumen 404. In at least some embodiments, the lead 300 may include one or more outer coatings of material 410 disposed over the outer surface 408 of multi-lumen conductor guide 402.

The central lumen 404 may be configured and arranged to receive a stylet. As discussed above, the stylet can be used for assisting in insertion and positioning of the lead 400 in the patient's body, and can be removed after the lead is implanted. The plurality of conductor lumens 406 are configured and arranged to receive conductors, which electrically couple the electrodes (134 of FIGS. 1, 2A, and 2B) to the terminals (310 of FIGS. 3A and 3B). FIG. 4B is a transverse cross-sectional view of one embodiment of conductors, such as conductor 420, disposed in the conductor lumens 406. In at least some embodiments, insulation 422 is disposed around the conductors 420 to prevent short-circuiting of the conductors 420.

Figure 5A:
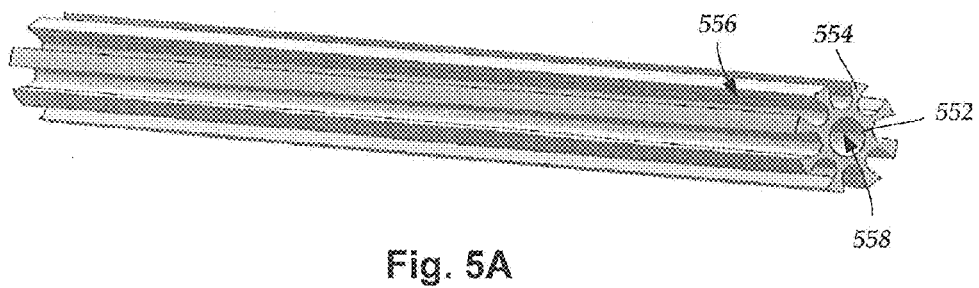
FIG. 5A is a schematic side perspective view of one embodiment of an end conductor guide, according to the invention.

A separate conductor guide can be provided one or both ends of the lead to, for example, facilitate manufacture or to alter properties (e.g., stiffness) at the ends of the lead or any combination of these factors. FIG. 5A illustrates one embodiment of an end conductor guide 550 that includes a central core 552 and a central lumen 558 which extends longitudinally through the central core 552 along the length of the end conductor guide 550. Multiple protrusions 554 extend radially outwards from the central core 552 to define conductor tracks 556 in the space between adjacent protrusions 554 of the end conductor guide 550. The central lumen 558 may be arranged to receive a stylet that can be used for assisting in insertion and implanting the lead in the patient's body.

In the illustrated embodiment, the central core 552 and the central lumen 558 have a circular cross-section. In other embodiments, the central core 552 or the central lumen 558 (or both) can have an elliptical, oval, or any other regular or irregular cross-sectional shape.

The multiple protrusions 554 extend longitudinally, parallel to the longitudinal axis of the end conductor guide 550 and are arranged circumferentially about the central core 552. In the illustrated embodiment, there are eight such protrusions arranged circumferentially and defining eight conductor tracks 556 between each pair of adjacent protrusions 554. The protrusions 554 give the end conductor guide 550 a star-shaped or cog-shaped cross-section, as illustrated, for example, in FIG. 6. The cog-shaped cross-sectional structure may also extend the entire longitudinal length of the end conductor guide 550, as illustrated in FIG. 5A, or may be confined to a portion of the end conductor guide 550, as illustrated, for example, in FIG. 8.

Any suitable number of protrusions 554 can be disposed on the end conductor guide 550, including, for example, four, five, six, seven, eight, nine, ten, twelve, sixteen, twenty, twenty-four, or more protrusions 554. In at least some embodiments, the number of protrusions depends on the number of conductors (not shown) in the electrical stimulation lead.

The conductor tracks 556 extend longitudinally along the length of the end conductor guide 550, and are configured to receive the conductors (see FIG. 5C) and separating the conductors from one another. In at least some embodiments, the number of the conductor tracks 556 equals the number of the conductors. As an example, the illustrated lead of FIGS. 5A-5E has eight conductors and eight conductor tracks 556.

In the illustrated embodiment of FIG. 5A, the conductor tracks 556 extend the entire longitudinal length of the end conductor guide 550.

The end conductor guide 550 can be formed using any stiff, biocompatible material. Examples of suitable materials include, but are not limited to, silicone, polyurethane, polyetheretherketone (PEEK), polyvinyl chloride, epoxy and the like, as well as combinations thereof. In at least some embodiments, the end conductor guide 550 is formed of a material that can reflow to promote structural integrity of the array of electrodes and terminals.

Figure 5B:
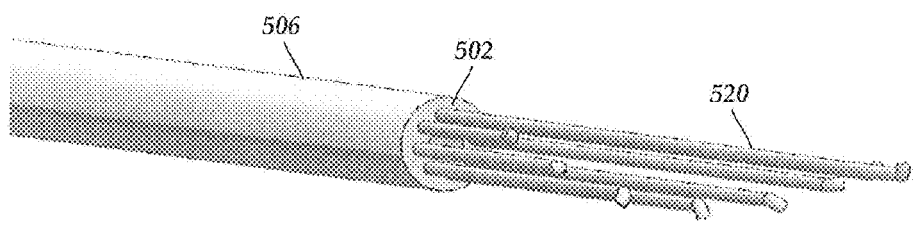
FIG. 5B is a schematic side perspective view of one embodiment of a portion of lead with conductors extending therefrom, according to the invention.
Figure 5C:
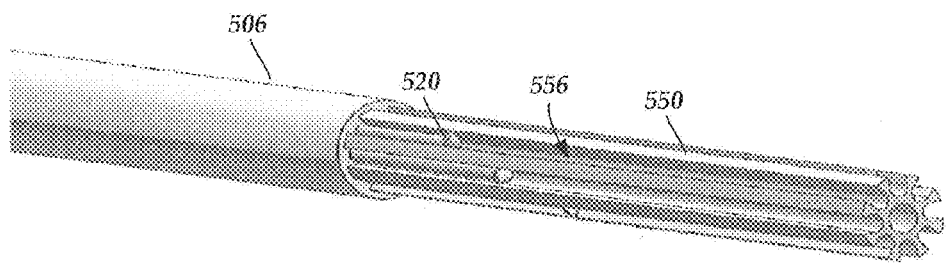
FIG. 5C is a schematic side perspective view of the portion of lead of FIG. 5B and the end conductor guide of FIG. 5A, according to the invention.

FIG. 5B illustrates one embodiment of a portion of an electrical stimulation lead with multiple conductors 520 extending outwards from the lead body 506 of the electrical stimulation lead. The electrical stimulation lead includes a lead body 506 with an elongated multi-lumen conductor guide 502 disposed therein. The multi-lumen conductor guide 502 has multiple conductor lumens (see, for example, FIG. 4A) arranged and positioned around a central lumen. The end conductor guide 550 can be disposed adjacent to an end of the electrical stimulation lead, as illustrated in FIG. 5C. For example, the distal end of the end conductor guide 550 can be positioned adjacent to the proximal end of the multi-lumen conductor guide 502. In at least some embodiments, the central lumen of the multi-lumen conductor guide 502 is in fluid communication with the central lumen 558 of the end conductor guide 550 to, for example, permit a stylet to pass from one central lumen to the other.

A portion of each of the conductors 520 is disposed within the conductor lumens (such as 406 in FIG. 4A) of the multi-lumen conductor guide 502, as shown in FIG. 5B. Each of the conductors 520 extends longitudinally outwards from a specific conductor lumen, away from the lead body 506. Each such conductor 520 is disposed within a specific conductor track 556 of the end conductor guide 550, as shown in FIG. 5C.

In at least some embodiments, stiffness or durometer (or both) of the end conductor guide 550 and the multi-lumen conductor guide 502 may differ. In one embodiment, the material of the end conductor guide 550 is stiffer with higher durometer as compared to that of the multi-lumen conductor guide 502, thereby, providing increased strength and durability to the proximal portion or the distal portion (whichever contains the end conductor guide) of the electrical stimulation lead. In other embodiments, the stiffness and durometer of the end conductor guide 550 and the multi-lumen conductor guide 502 are the same.

Figure 5D:
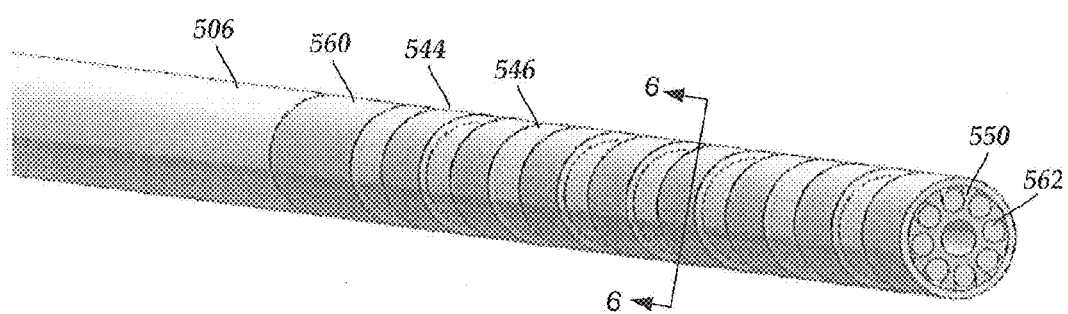
FIG. 5D is a schematic side perspective view of one embodiment of the arrangement of FIG. 5C with a retention sleeve, contacts, and spacers added, according to the invention.

FIG. 5D illustrates a retention sleeve 560, contacts (terminal or electrodes) 544, and spacers 546 disposed over the conductor guide 550. Each of the conductors 520 is disposed in the conductor track 556 of the end conductor guide 550. A hollow ring shaped retention sleeve 560 is optionally disposed on the lead. Spaced apart from the retention sleeve 560, ring shaped contacts (terminal or electrode) 544 are positioned in an array. Each contact 544 is welded or otherwise electrically coupled to one of the conductors 520 traversing the conductor tracks 556 of the end conductor guide 550. A cross-sectional view of this arrangement is illustrated in FIG. 6.

The retention sleeve 560 can be formed using any biocompatible material. Examples of suitable materials include metals, alloys, and the like, as well as combinations thereof. The retention sleeve 560 can be useful for securing the lead in a connector of a control module or lead extension. For example, a screw (see FIG. 3B) or other retaining element can be provided with the connector (for example, connector 322 of FIG. 3B) and can be tightened against the retention sleeve 560 to retain the electrical stimulation lead in the connector. The illustrated retention sleeve 560 is a ring-shaped element. However, in other embodiments, the retention sleeve 560 has an elliptical, oval, or other cross-sectional shape.

The contacts 544 of the electrical stimulation lead can be either electrodes or terminals. In at least some embodiments, when the contacts 544 are disposed at the distal end of the electrical stimulation lead, the contacts 544 are electrodes, and when disposed at the proximal end of the electrical stimulation lead, the contacts 544 are terminals may be disposed to serve as conductive contacts. Non-conductive pacers 546 are disposed between adjacent contacts 544.

Once the conductors 520 are appropriately arranged in the conductor track 556 of the end conductor guide 550, a remaining portion of the conductor track 556 is optionally filled by a non-conductive filler material 562. The remaining portion in the conductor track 556 is an open space, unoccupied by the conductors 520. For instance, in a case where the end conductor guide 550 is disposed at the proximal end of the lead body 506, portion filled by the non-conductive filler material 562 is proximal to the weld in the conductor track 556. Such filling by the non-conductive filler material 562 can be done prior to, or after, the welding of the contact 544 to the conductor 520 placed in the conductor track 556. The non-conductive filler material 562 can be formed from any suitable material, such as polyurethane, silicone, and the like, and combinations thereof and may be a monofilament material. In at least some embodiments, the non-conductive filler material 562 is a material that can reflow during a reflow process.

Figure 5E:
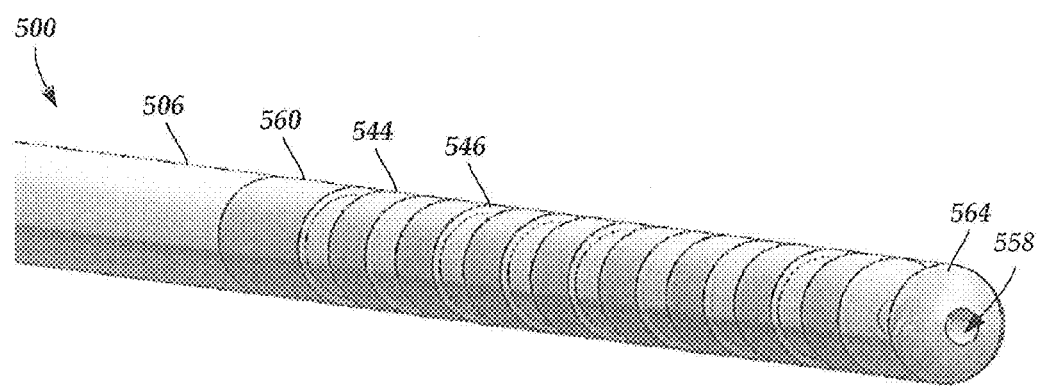
FIG. 5E is a schematic side perspective view of one embodiment of the arrangement of FIG. 5D with a tip added, according to the invention.

In at least some embodiments, a non-conductive tip 564 is mounted on a terminal end of the end conductor guide 550, as shown in FIG. 5E. The non-conductive tip 564 optionally includes a central lumen (particularly if the end conductor guide 550 is on the proximal end of the lead) that extends to the central lumen 558 of the end conductor guide 550. In at least some embodiments, a stylet can be inserted through the central lumen of the non-conductive tip 564 to the central lumen 558 of the end conductor guide 550. In at least some embodiments, the shape of the non-conductive tip 564 depends on the shape of the end conductor guide 550 or the lead body 506.

The non-conductive tip 564 can be formed from any non-conductive, biocompatible material. Examples of suitable materials include polyurethane, silicone, or the like, as well as combinations thereof.

One method of making the electrical stimulation lead 500 includes positioning terminal portions of each of the conductors 520 in the conductor tracks 556 of the end conductor guide 550. Multiple contacts 544 are arranged over the end conductor guide 550, and each of the terminal portions of the multiple conductor tracks 556 is coupled to at least one of the contacts 544. The non-conductive spacers 546 are positioned between adjacent contacts 544 of the electrical stimulation lead 500. Finally, the optional non-conductive tip 564 is attached to the end of the end conductor guide 550, to assemble the electrical stimulation lead 500.

Figure 7A:
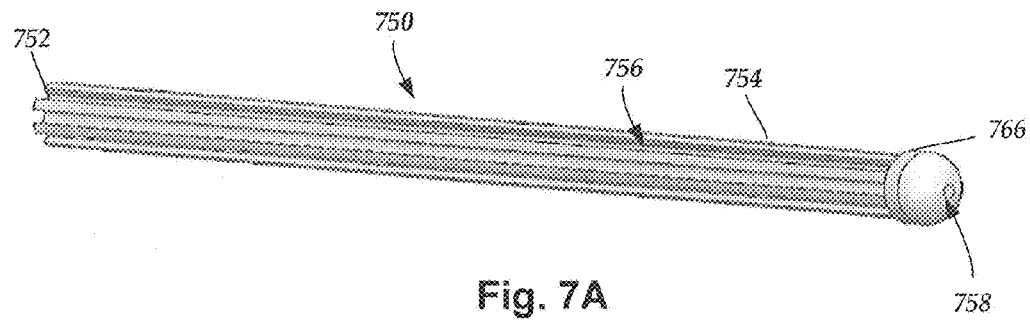
FIG. 7A is a schematic side perspective view of a second embodiment of an end conductor guide, according to the invention.
Figure 7B:
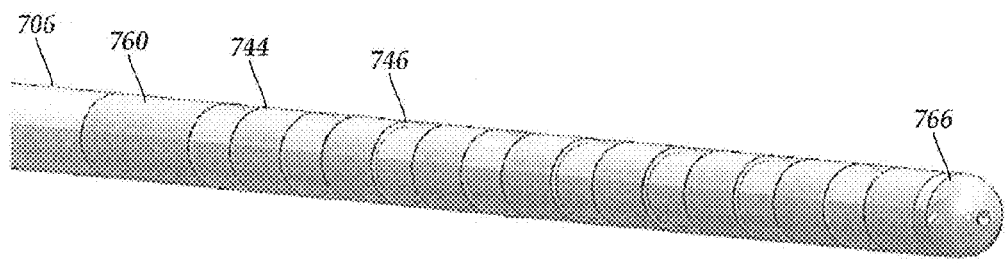
FIG. 7B is a schematic side perspective view of one embodiment of an end of lead incorporating the end conductor guide of FIG. 7A, according to the invention.

In at least some other embodiments, a tip 766 can be part of the end conductor guide 750, as illustrated in FIG. 7A, instead of added during manufacture as illustrated in FIG. 5E. The tip 766 has a central lumen 758. The end conductor guide 750 has a central core 752 and a number of protrusions 754 extending outward from the central core 752 of the end conductor guide 750. A number of conductor tracks 756 are defined between adjacent protrusions 754 of the end conductor guide 750. The end conductor guide 750 is attached the terminal portion of the lead body 706, as shown in FIG. 7B. A retention sleeve 760, contacts 744, and spacers 746 are disposed on the end conductor guide 750.

Figure 8:
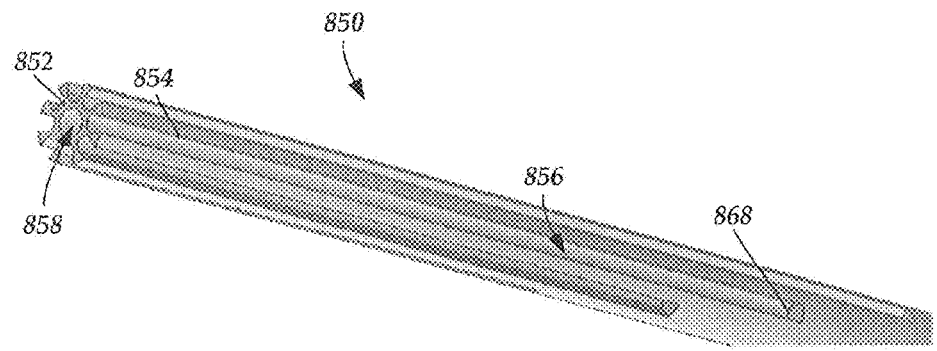
FIG. 8 is a schematic side perspective view of a third embodiment of an end conductor guide, according to the invention.

FIG. 8 illustrates another embodiment of an end conductor guide 850. The end conductor guide 850 includes a central core 852 and a central lumen 858 extending from the central core 852. A number of conductor tracks 856 disposed in a space between adjacent protrusions 854, are arranged around the central lumen 858 of the end conductor guide 850.

Each of the conductor tracks 856 extends a different distance along the length of the end conductor guide 850. Each of the conductor tracks 856 have their terminal portions 868 terminating at different points. In at least some embodiments, the different distances of the conductor tracks 856 are representative of the different attachment sites of the various conductors with the contacts. For example, the lead body 506 and conductors 520 of FIG. 5B can be combined with the end conductor guide 850 so that the conductors extend along the conductor tracks 856 with each conductor terminating (and attaching to a contact (not shown)) near a terminal portion 868 of the respective conductor track 856. In these embodiments, the conductor tracks 856 are substantially filled by the conductors 520 so there may be no need to add filling material to the conductor tracks in contrast to other embodiments described above. In the depicted embodiment, since the conductor tracks 856 terminate at different points along the longitudinal length of the end conductor guide 850, it can be seen that the end conductor guide 850 has a cog-shaped or star-shaped cross-section only at one end.

Figure 9:
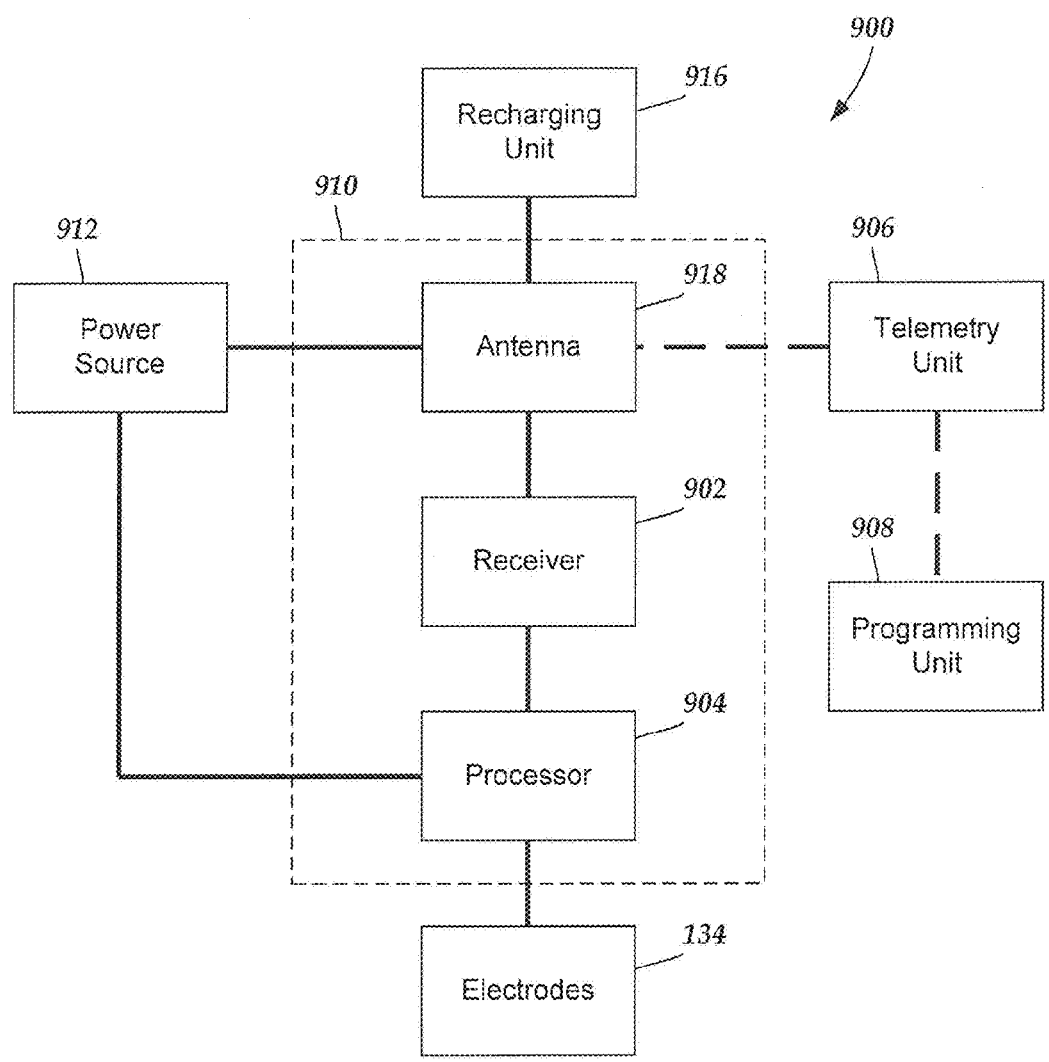
FIG. 9 is a schematic overview of one embodiment of components of a stimulation system, including an electronic subassembly disposed within a control module, according to the invention.

FIG. 9 is a schematic overview of one embodiment of components of an electrical stimulation system 900 including an electronic subassembly 910 disposed within a control module. It will be understood that the electrical stimulation system can include more, fewer, or different components and can have a variety of different configurations including those configurations disclosed in the stimulator references cited herein.

Some of the components (for example, power source 912, antenna 918, receiver 902, and processor 904) of the electrical stimulation system can be positioned on one or more circuit boards or similar carriers within a sealed housing of an implantable pulse generator, if desired. Any power source 912 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 918 or a secondary antenna. The external power source can be in a device that is mounted on the skin of the user or in a unit that is provided near the user on a permanent or periodic basis.

If the power source 912 is a rechargeable battery, the battery may be recharged using the optional antenna 918, if desired. Power can be provided to the battery for recharging by inductively coupling the battery through the antenna to a recharging unit 916 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 904 is generally included to control the timing and electrical characteristics of the electrical stimulation system. For example, the processor 904 can, if desired, control one or more of the timing, frequency, strength, duration, and waveform of the pulses. In addition, the processor 904 can select which electrodes can be used to provide stimulation, if desired. In some embodiments, the processor 904 may select which electrode(s) are cathodes and which electrode(s) are anodes. In some embodiments, the processor 904 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 908 that, for example, allows modification of pulse characteristics. In the illustrated embodiment, the processor 904 is coupled to a receiver 902 which, in turn, is coupled to the optional antenna 918. This allows the processor 904 to receive instructions from an external source to, for example, direct the pulse characteristics and the selection of electrodes, if desired.

In one embodiment, the antenna 918 is capable of receiving signals (e.g., RF signals) from an external telemetry unit 906 which is programmed by a programming unit 908. The programming unit 908 can be external to, or part of, the telemetry unit 906. The telemetry unit 906 can be a device that is worn on the skin of the user or can be carried by the user and can have a form similar to a pager, cellular phone, or remote control, if desired. As another alternative, the telemetry unit 906 may not be worn or carried by the user but may only be available at a home station or at a clinician's office.

The programming unit 908 can be any unit that can provide information to the telemetry unit 906 for transmission to the electrical stimulation system 900. The programming unit 908 can be part of the telemetry unit 906 or can provide signals or information to the telemetry unit 906 via a wireless or wired connection. One example of a suitable programming unit is a computer operated by the user or clinician to send signals to the telemetry unit 906.

The signals sent to the processor 904 via the antenna 918 and receiver 902 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 900 to cease operation, to start operation, to start charging the battery, or to stop charging the battery. In other embodiments, the stimulation system does not include an antenna 918 or receiver 902 and the processor 904 operates as programmed.

Optionally, the electrical stimulation system 900 may include a transmitter (not shown) coupled to the processor 904 and the antenna 918 for transmitting signals back to the telemetry unit 906 or another unit capable of receiving the signals. For example, the electrical stimulation system 900 may transmit signals indicating whether the electrical stimulation system 900 is operating properly or not or indicating when the battery needs to be charged or the level of charge remaining in the battery. The processor 904 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An electrical stimulation lead extending from a proximal end to a distal end and having a circumference, the lead comprising:
   an end conductor guide disposed at the proximal or distal end of the lead, the end conductor guide having a first end, a second end, a generally cylindrical shape, a length, and an exterior surface, the end conductor guide defining a plurality of conductor tracks formed in the exterior surface and extending longitudinally from the first end at least partway along the length of the end conductor guide, the end conductor guide further defining protrusions between adjacent conductor tracks giving the end conductor guide a cog-shaped cross-section at the first end, wherein each of the conductor tracks extends a different distance along the length of the end conductor guide;

a plurality of electrodes disposed along the distal end of the lead, wherein each electrode is a cylindrical ring electrode extending around the circumference of the lead;

a plurality of terminals disposed along the proximal end of the lead, wherein each terminal is a cylindrical ring terminal extending around the circumference of the lead, wherein the plurality of terminals are disposed over the end conductor guide when the end conductor guide is disposed at the proximal end of the lead and the plurality of electrodes are disposed over the end conductor guide when the end conductor guide is disposed at the distal end of the lead;

an elongated lead body extending from the plurality of electrodes to the plurality of terminals; and a plurality of conductors coupling the plurality of electrodes to the plurality of terminals, each of the conductors comprising an end portion that is disposed within one of the plurality of conductor tracks of the end conductor guide.

2. The electrical stimulation lead of claim 1, wherein each of the conductor tracks extends only partway along the length of the end conductor guide.

3. The electrical stimulation lead of claim 1, wherein the end conductor guide defines a central lumen extending longitudinally through the end conductor guide.

4. The electrical stimulation lead of claim 1, wherein the lead body comprises a multilumen conductor guide and an outer layer disposed over the multilumen conductor guide, the multilumen conductor guide comprising a central lumen and a plurality of conductor lumens disposed around the central lumen, wherein a portion of each of the plurality of conductors is disposed within one of the conductor lumens.

5. The electrical stimulation lead of claim 4, wherein the multilumen conductor guide has an end that is disposed adjacent the end conductor guide.

6. A system for electrical stimulation of patient tissue, the system comprising:
the electrical stimulation lead of claim 1; and
a control module coupleable to the electrical stimulation lead.

7. The system of claim 6, further comprising a lead extension having a proximal end and a distal end, the lead extension comprising
a connector disposed on the distal end of the lead extension and configured and arranged to receive the proximal end of the electrical stimulation lead;
an end conductor guide disposed at the proximal end of the lead extension, the end conductor guide having a first end, a second end, a generally cylindrical shape, a length, and an exterior surface, the end conductor guide defining a plurality of conductor tracks formed in the exterior surface and extending longitudinally from the first end at least partway along the length of the end conductor guide, the end conductor guide further defining protrusions between adjacent conductor tracks giving the end conductor guide a cog-shaped cross-section at the first end;
a plurality of contacts disposed along the proximal end of the lead extension over the end conductor guide of the lead extension;
an elongated lead extension body extending from the connector to the plurality of contacts; and
a plurality of conductors coupling the connector to the plurality of contacts, each of the conductors comprising an end portion that is disposed within one of the plurality of conductor tracks of the end conductor guide.

8. A method of making the electrical stimulation lead of claim 1, the method comprising:
providing the end conductor guide;
disposing the end portions of each of the plurality of conductors in the conductor tracks of the end conductor guide;
disposing a plurality of contacts over the end conductor guide;
coupling the end portions of the conductors to the plurality of contacts; and
disposing insulative spacers between adjacent contacts.

9. The method of claim 8, further comprising attaching a non-conductive tip to an end of the end conductor guide.

10. The method of claim 8, wherein the end conductor guide comprises a non-conductive tip portion.

11. The electrical stimulation lead of claim 4, wherein the end conductor guide and the protrusions are formed of a stiffer material than a material forming the multilumen conductor guide.

12. The electrical stimulation lead of claim 4, wherein the end conductor guide and the protrusions are formed of a material with a higher durometer than a material forming the multilumen conductor guide.

13. The stimulation lead of claim 1, wherein the end conductor guide defines a number of the conductor tracks equal to a number of the conductors.

14. The stimulation lead of claim 1, wherein the end conductor guide is disposed only at the distal end of the lead and defines a number of the conductor tracks equal to a number of the electrodes.

15. The stimulation lead of claim 1, wherein the end conductor guide is disposed only at the proximal end of the lead and defines a number of the conductor tracks equal to a number of the terminals.

16. The stimulation lead of claim 1, wherein the lead body comprises a closed, non-conductive tip disposed at the second end of the end conductor guide.

17. The stimulation lead of claim 1, wherein the end conductor guide is disposed only on the proximal end of the lead.

18. The stimulation lead of claim 1, wherein the protrusions are arranged uniformly around a circumference of the end conductor guide.

19. The stimulation lead of claim 1, wherein the lead body and either the electrodes or the terminals completely cover the end conductor guide.

* * * * *